US007767991B2

(12) United States Patent
Sacchetti

(10) Patent No.: US 7,767,991 B2
(45) Date of Patent: Aug. 3, 2010

(54) METHOD OF OPERATING AN INFRARED DRIP SENSOR IN AN ENTERAL PUMP SYSTEM TO REDUCE FALSE ALARM CONDITIONS

(75) Inventor: Peter J. Sacchetti, Attleboro, MA (US)

(73) Assignee: OST Medical, Inc., Warwick, RI (US)

( * ) Notice: Subject to any disclaimer, the term of this patent is extended or adjusted under 35 U.S.C. 154(b) by 226 days.

(21) Appl. No.: 11/954,002

(22) Filed: Dec. 11, 2007

(65) Prior Publication Data
US 2008/0139997 A1 Jun. 12, 2008

Related U.S. Application Data

(60) Provisional application No. 60/869,386, filed on Dec. 11, 2006.

(51) Int. Cl.
G01N 15/06 (2006.01)
(52) U.S. Cl. .................... 250/573; 250/577
(58) Field of Classification Search ............ 250/221, 250/573, 574, 576, 205, 338.1, 338.4, 353; 340/606, 578–583; 604/28–34, 65, 189–207, 604/503–511; 128/DIG. 13, 200.16; 600/65, 600/67, 432; 73/293, 313
See application file for complete search history.

(56) References Cited

U.S. PATENT DOCUMENTS

| 3,500,366 | A |   | 3/1970  | Chesney et al      |
|-----------|---|---|---------|--------------------|
| 4,038,982 | A | * | 8/1977  | Burke et al. ...... 604/65 |
| 4,126,132 | A |   | 11/1978 | Portner et al.     |
| 4,314,484 | A |   | 2/1982  | Bowman             |
| 4,504,263 | A |   | 3/1985  | Steuer et al.      |
| 4,608,042 | A |   | 8/1986  | Vanderveen et al.  |
| 4,845,487 | A |   | 7/1989  | Frantz et al.      |
| 5,186,057 | A |   | 2/1993  | Everhart           |
| 5,374,251 | A |   | 12/1994 | Smith              |
| 5,415,641 | A |   | 5/1995  | Yerlikaya et al.   |
| 5,750,998 | A |   | 5/1998  | Goldman            |
| 6,118,526 | A |   | 9/2000  | Hidalgo et al.     |
| 6,120,475 | A |   | 9/2000  | Chen               |
| 6,199,603 | B1|   | 3/2001  | DiGianfilippo et al.|
| 7,169,128 | B2|   | 1/2007  | Kriesel et al.     |
| 7,256,888 | B2|   | 8/2007  | Staehr et al.      |
| 2007/0112323 | A1 |  | 5/2007  | Daly             |
| 2007/0142777 | A1 |  | 6/2007  | Klein            |

* cited by examiner

*Primary Examiner*—Que T Le
(74) *Attorney, Agent, or Firm*—Barlow, Josephs & Holmes, Ltd.

(57) ABSTRACT

The present invention provides a method of operating an infrared drip sensor in an enteral pump system to reduce false alarm conditions. The method consists of the following steps: optically coupling a infrared beam emitter with an infrared beam detector along an infrared beam path that extends through a drip chamber and intersects the drip path; monitoring the output signal of the infrared beam detector to detect pulses; monitoring the pulses for an interruption thereof; and running an infrared beam power update routine when an interruption is detected in the pulses, the infrared beam power update routine consisting of incrementally increasing a power level of the infrared beam until the power level of the infrared beam is sufficient to re-establish an output signal at the infrared beam detector.

2 Claims, 5 Drawing Sheets

METHOD OF OPERATING AN INFRARED DRIP SENSOR IN AN ENTERAL PUMP SYSTEM TO REDUCE FALSE ALARM CONDITIONS

CROSS-REFERENCE TO RELATED APPLICATION

This application is related to and claims priority from earlier filed provisional patent application Ser. No. 60/869,386, filed Dec. 11, 2006.

BACKGROUND OF THE INVENTION

The present invention relates to enteral pumps for delivering liquid nutrition to patients who are unable to eat.

Enteral feeding pumps are used to supply liquid nutrition to patients who are unable to eat. The pumping system generally consists of the pump and a disposable tubing set for delivery of the liquid nutrition. The tubing set is connected between a bag of liquid nutrition and a patient's gastric line. A section of the tubing set is seated on the pump housing where a rotor draws fluid through the tubing set by peristaltic action.

A common design feature of enteral pumps is the ability to detect the presence or absence of liquid flowing through the tube set. This is typically accomplished by the detection of drops falling within a transparent drip chamber portion of the tubing set. In this regard, the transparent drip chamber is seated within an opening in the pump housing where an infrared (IR) light source (light emitting diode—LED) and infrared detector are positioned on opposing sides of the drip chamber transverse to the liquid flow. The IR beam passes through the drip chamber. When a drop of liquid falls, it interrupts the IR beam and this interruption is converted to an electronic pulse. The pulse presence and frequency are processed by the pump firmware, which then either allows continuing pump operation or stops the pump indicating one of several possible alarm conditions, such as occlusion or excessive flow.

For the drop detection system to operate reliably, the IR beam intensity must be set to a level that is sufficient to "see" through the drip chamber walls, but not so intense that that the beam is detected through the water drops without producing a detection pulse. The IR beam power level is optimized for water, since excess power can cause the water to be transparent to the infrared beam, i.e. the beam is strong enough to pass right through the water drop. Liquid nutrient is more optically opaque and thus it can be detected with a wider tolerance of beam power level. Because of this, water is the "standard" for calibration of the detection power. For current pump design, the beam power level is set to a fixed value that is intended to accommodate all variations in electronics and materials used in the beam path.

False alarms are an undesirable consequence of fixed sensitivity when the transparent wall of the drip chamber may become less transparent through the accumulation of liquid residue or droplets. These droplets are only a problem when they are located in the path of the IR beam. Given enough operating time, it is probable that a droplet will be situated in this manner. This issue is more problematic for water due to its propensity for droplet formation due to its high surface tension. Liquid nutrient has a relatively lower surface tension and droplets dissipate more readily once they impinge on the chamber wall. Water however, has a tendency to stay in place longer and thus create a blocking condition. With fixed infrared detector sensitivity, water droplets will cause false alarms.

Typically, enteral pumps deliver only liquid nutrient to the patient. In addition to the liquid nutrient, caregivers must also give water to the patient, as the liquid nutrient contains insufficient water for normal dietary requirements.

Several enteral pump manufacturers have produced pumps, which are capable of pumping both liquid nutrient and water from separate containers. A typical prior art design uses two separately programmable peristaltic pumping motors, which are activated according to a user program. Another method uses a single peristaltic pump, and a tubing set having an integral two-way valve. This valve is actuated by a second motor on the pump, and thus controls that liquid source. Both of these configurations are relatively high in cost because of the multiple motors.

In view of the foregoing, there is a desire for a less expensive enteral pump system that includes only a single motor as well as a method of operating an infrared drip sensor in an enteral pump system to reduce occurrence of false alarms. It is also desirable to provide a method of operating the infrared drip sensor that automatically adjusts the infrared beam power according to the current optical conditions. Further it is desirable to have a method of automatically adjusting the infrared beam power of an enteral pump system to accommodate water droplets and residue within the drip chamber. Even further still it is desirable to have a method of operating a drip sensor that can automatically distinguish between water flow and liquid nutrient flow.

BRIEF SUMMARY OF THE INVENTION

The present invention preserves the well known advantages of prior methods of operating an infrared drip sensor in an enteral system but, in addition, provides new advantages not found in currently available methods and overcomes many disadvantages of the currently available methods for operating an infrared drip sensor.

The present invention provides a method of operating an infrared drip sensor in an enteral pump system to reduce false alarm conditions. The method consists of the following steps: providing a drip chamber; operating a pump to move a fluid to the drip chamber wherein the fluid drips through the drip chamber along a drip path; optically coupling a infrared beam emitter with an infrared beam detector along an infrared beam path that extends through the drip chamber and intersects the drip path, the infrared beam emitter emitting an infrared beam, the infrared detector generating an output signal responsive to the presence of the infrared beam as the fluid drips through the drip chamber; setting an initial power level of the infrared beam; monitoring the output signal of the infrared beam detector as the fluid drips through the drip chamber so as to detect pulses in the output signal level, the pulses representing the fluid dripping through the drip chamber; monitoring the pulses for an interruption thereof; running an infrared beam power update routine when an interruption is detected in the pulses, the infrared beam power update routine consisting of incrementally increasing a power level of the infrared beam until the power level of the infrared beam is sufficient to re-establish an output signal at the infrared beam detector; shutting off the motor for pumping when the output signal cannot be reestablished after the infrared beam power update routine; and triggering an alarm when the output signal cannot be re-established after the infrared beam power update routine.

The present invention also provides a method for automatic adjustment of the pumping rate of an enteral pump system according to the type of fluid flowing through the pump system, the method comprising the following steps: providing a first opaque fluid and a second clear fluid for pumping; providing an enteral tubing system that first allows flow of the first fluid and then flow of the second fluid upon exhaustion of the first fluid; providing a drip chamber; operating a pump at a first pumping rate appropriate for the first fluid to move the first fluid to the drip chamber wherein the first fluid drips through the drip chamber along a drip path; optically coupling a infrared beam emitter with an infrared beam detector along an infrared beam path that extends through said drip chamber and intersects said drip path, said infrared beam emitter emitting an infrared beam, said infrared beam detector generating an output signal responsive to the presence of the infrared beam as the first fluid drip through the drip chamber, setting an initial power level of the infrared beam; monitoring the output signal of the infrared beam detector as the fluid drips through the drip chamber so as to detect pulses in the output signal level, the pulses representing the first fluid dripping through the drip chamber; at predetermined time intervals, detecting the type of fluid being pumped by running a fluid type check routine consisting of: counting a first number of pulses in a predetermined period of time, increasing the power level of the infrared beam by a predetermined amount, and counting a second number of pulses in the same predetermined period of time, wherein a comparison of said number of pulses determines fluid type; operating the pump such that when the second number of pulses is equal to said first number of pulses, said first pumping rate is maintained, and further such that when the number of pulses are unequal, said first pumping rate is changed to a second pumping rate appropriate for the second fluid.

It is therefore an object of the present invention to provide a method of operating an enteral pump with reduced occurrences of false alarms.

It is a further object of the present invention is to provide a method of automatically adjusting the infrared beam power of an enteral pump system to accommodate water droplets and residue within the drip chamber.

Yet another object of the present invention is to provide a method of operating a drip sensor to distinguish between water flow and liquid nutrient flow.

Other objects, features and advantages of the invention shall become apparent as the description thereof proceeds when considered in connection with the accompanying illustrative drawings.

BRIEF DESCRIPTION OF THE DRAWINGS

The novel features, which are characteristic of the method for operating an infrared drip sensor in an enteral system, are set forth in the appended claims. However, the method of operating an infrared drip sensor in an enteral system, together with further embodiments and attendant advantages, will be best understood by reference to the following detailed description taken in connection with the accompanying drawings in which:

DETAILED DESCRIPTION OF THE PREFERRED EMBODIMENTS

The present method solves a disadvantage of the prior art by providing a new and unique method 10 for operating a drip sensor system in an enteral pump system, which reduces false alarm conditions.

As described in the background, an enteral pumping system generally consists of a pump system 302 and disposable tubing set for delivery of the liquid nutrition. The tubing set is connected between a bag of liquid nutrition and a patient's gastric line. A section of the tubing set is seated on the pump housing where a rotor draws fluid through the tubing set by peristaltic action.

Figure 6:
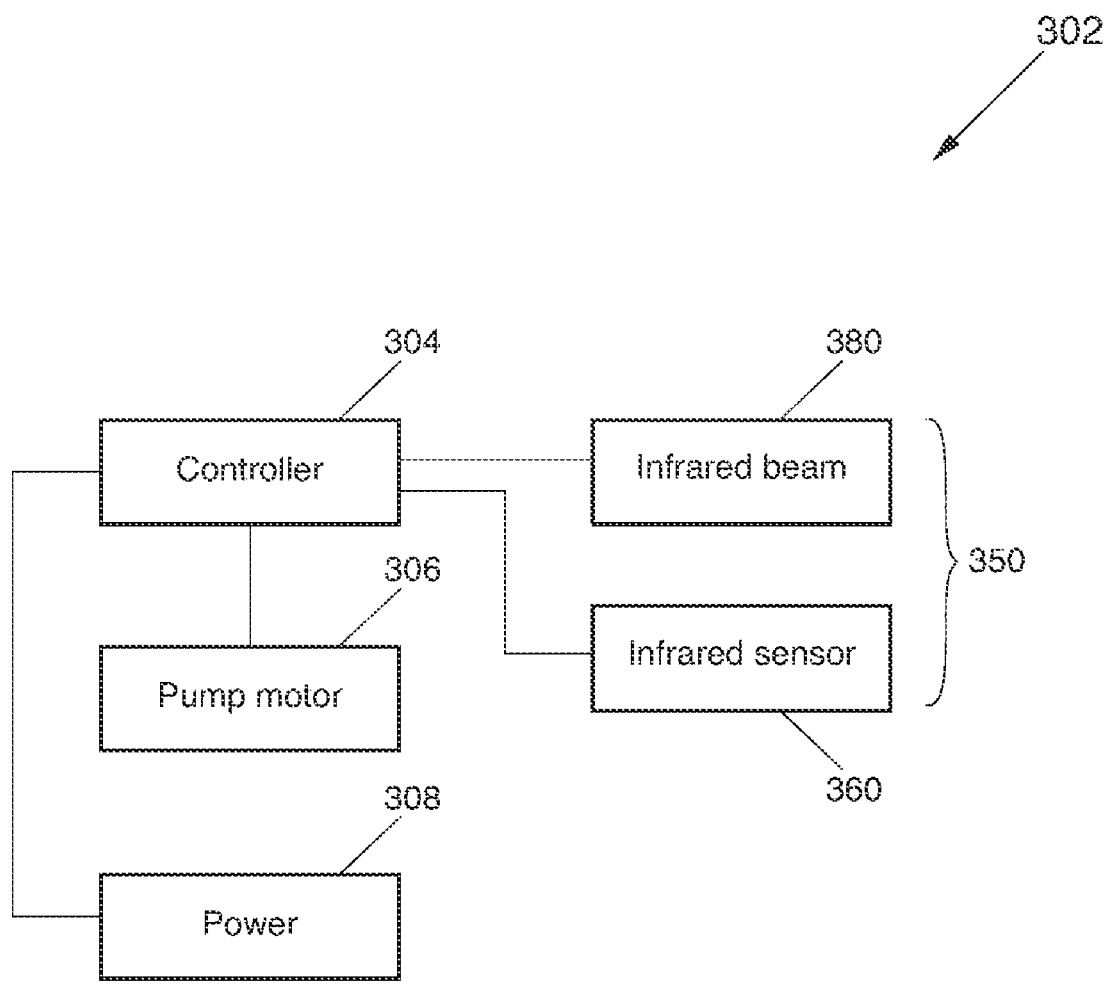

Generally, the pump system 302 comprises a controller 304, pump motor 306, power source 308, and an infrared sensor system 350 containing an infrared beam emitter 380 and infrared beam sensor 360. See FIG. 6. The controller 304 is powered by the power source 308 and controls the pump motor 306 and the infrared sensor system 305. More specifically, the controller 304 instructs the pump motor 306 when to switch off/on based upon an output signal received in the infrared beam sensor 360 which will be further described below.

Figure 1:
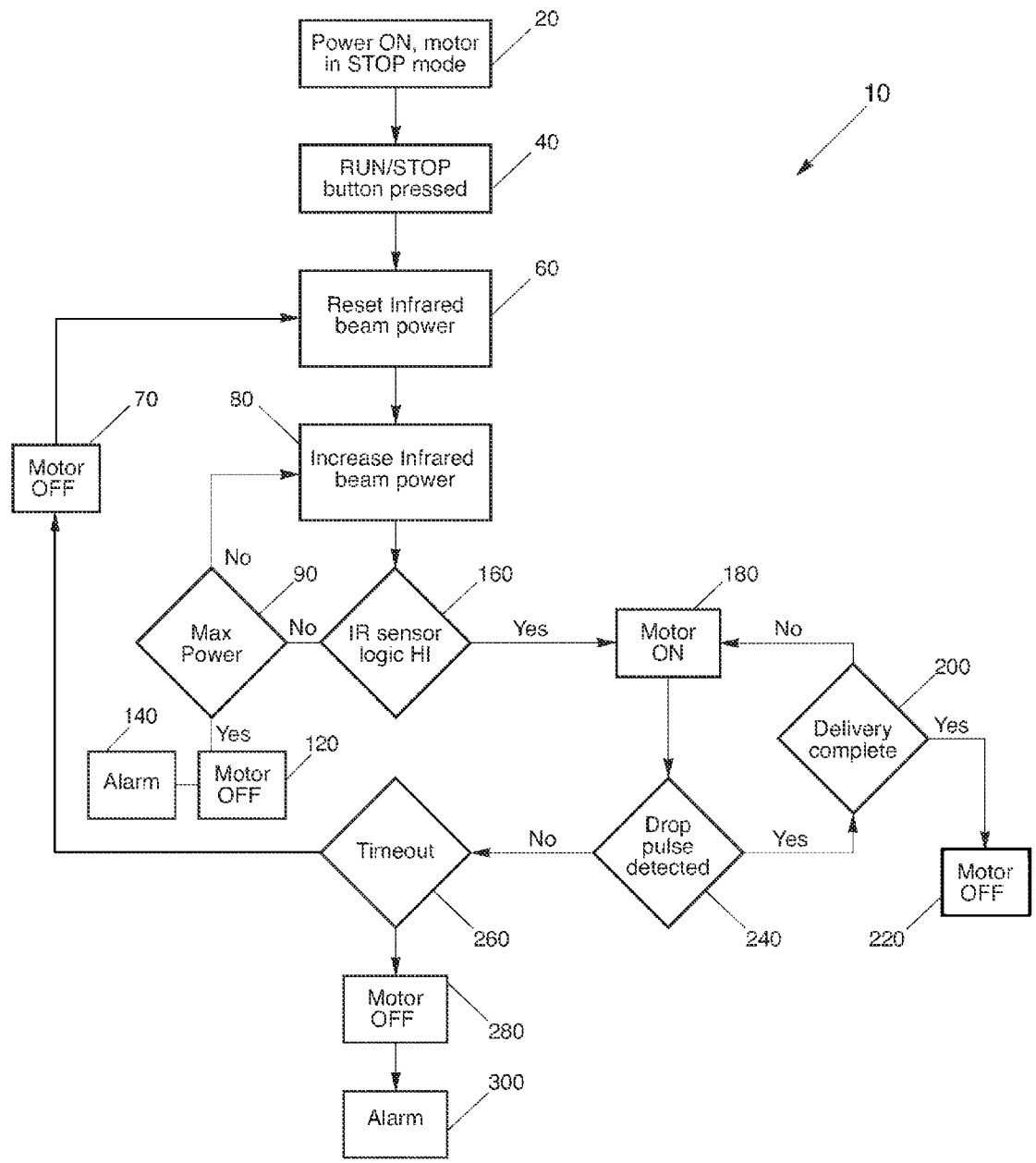
FIG. 1 is a flow chart of the method for operating an infrared drip sensor in an enteral pump system of the present invention.

Referring to FIG. 1, a flow chart of a method 10 of operation for the infrared drip sensor system in an enteral pump system is illustrated. The method 10 generally comprises the following steps as outlined below.

Figure 2:
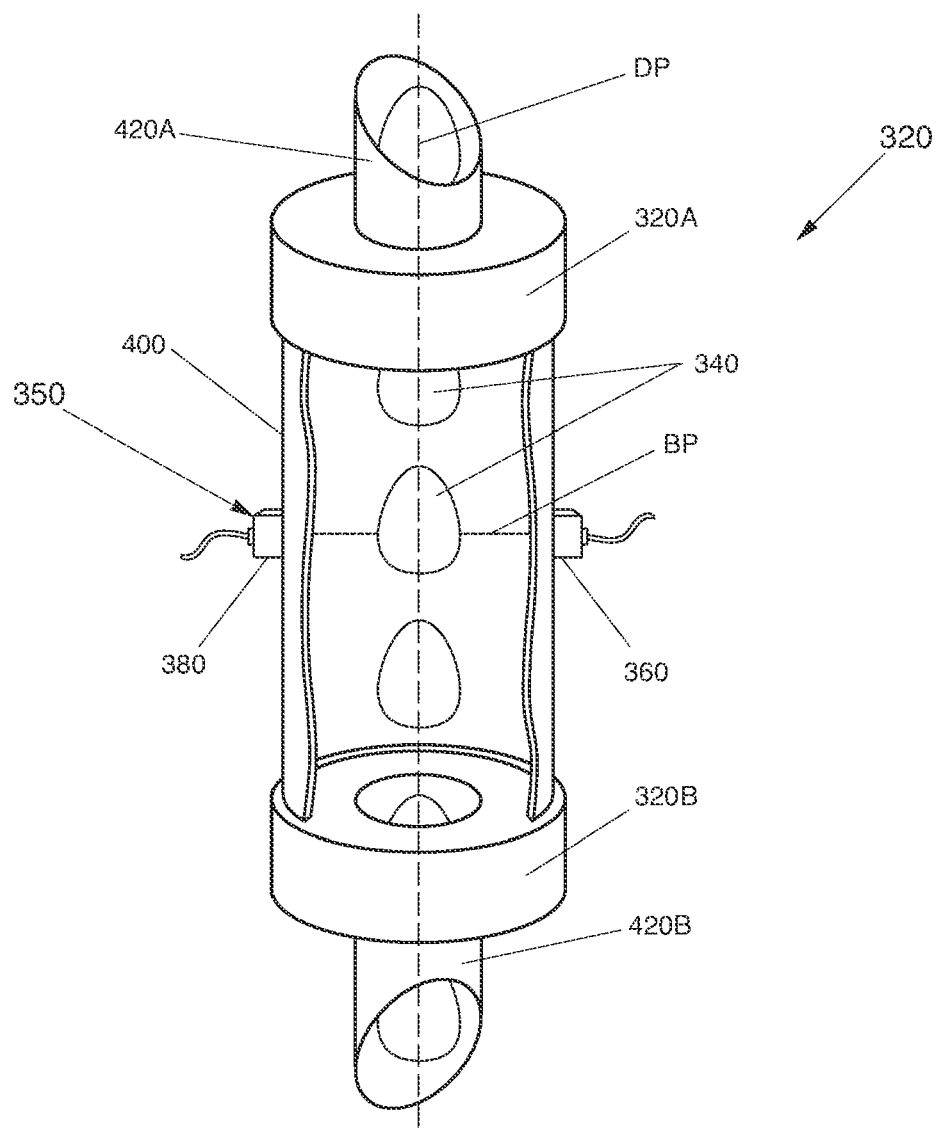
FIG. 2 is a cross-sectional view of a drip chamber used in the method of FIG. 1 with fluid dripping there through to intersect the infrared beam path.

Referring to FIG. 2, a tubing system 420 and a drip chamber 320 are provided. The tubing system 420A, 420B connects at a top end 320A and bottom end 320B of the drip chamber 320. The tubing system 420A, 420B is similar to those known in the prior art. As the pump 306 is operated, fluid 340 drips through the chamber 320. The drip chamber 320 contains a wall 400, which is of a thickness and color suitable for a penetration of an infrared beam. When fluid 340 flows through the chamber 320, the fluid moves along a defined drip path DP within the drip chamber.

Generally, the pump motor 306 has the capability of different programmed rates of pumping of different types of fluid 340 to the drip chamber 320. For example, some fluids with higher viscosity may require a higher pump rate while other fluids, like water, may require lower pump rate settings. The pump motor 306 also has a run/stop switch capable of controlling the power to the motor which pumps the fluid 340 through the tubing system 420A, 420B.

To begin operation of the pump 306, as shown in the method 10 of FIG. 1, the pump 306 is turned on with the pump motor 306 in stop mode 20. Next, the pump motor 306 is turned on to a run mode 40 to move the fluid to the drip chamber 320 wherein the fluid drips through the drip chamber 320 along the defined drip path DP. The fluid drips through the drip chamber 320 at a flow rate dependent upon the viscosity of the product, the configuration of the drip chamber 320, and the programmed pumping rate based upon the fluid flowing.

Figure 3:
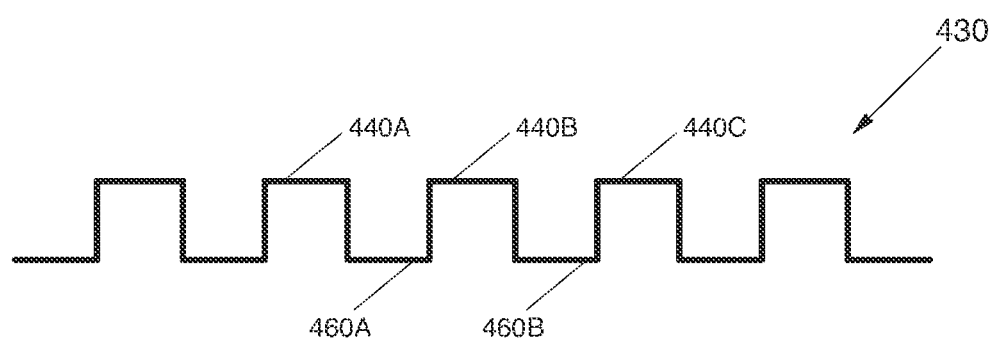
FIG. 3 is an illustration of the amplitude of the pulse wave during operation of the infrared drip sensor in FIG. 1.

Referring to FIG. 2, to measure the rate of drops through the drip chamber 320, an infrared sensor system 350 is used. The infrared sensor system 350 includes an infrared beam emitter 380 and an infrared beam detector 360, which are optically coupled along an infrared beam path BP that extends transversely through the drip chamber wall 400 and intersects the drip path DP. Referring back to FIG. 1, initially, the infrared beam power level is automatically stepped up to a level that penetrates the walls of the drip chamber 320. To calibrate the initial infrared beam power, the infrared level can be manually or automatically updated before each use. When the infrared beam emitter 380 emits an infrared beam, the infrared beam detector 360 generates an output signal 430 responsive to the presence of the infrared beam as the fluid 340 drips through the drip chamber 320. As will be explained further, a sample pulse wave of the output signal 430 is illustrated in FIG. 3.

After increasing an initial power level of the infrared beam 80, the output signal of the infrared beam detector 360 is monitored 160 as the fluid 340 drips through the drip chamber 320 so as to detect pulses in the output signal level 430. The pulses represent the fluid dripping through the drip chamber. As shown in FIG. 3, when the infrared beam emitter 380 emits an infrared beam, it establishes an output signal 430 in the infrared beam detector 360. At steady state operation, this is seen as a logic-hi 440A, 440B, 440C amplitude of the output signal 430. When the fluid 340 traveling along the drip path DP intersects the infrared beam path BP, it blocks the infrared beam and interrupts the output signal 430 in the beam detector 360. These interruptions are seen as a logic-low amplitude 460A, 460B. The pulsing of the amplitude from high to low means that fluid 340 is dripping through the chamber 320. For each infrared sensor logic-low amplitude 460A, 460B, there is a drop of fluid that passed along the drip path DP of the drip chamber 320 and intersected the beam path BP. By counting the number of sensor logic-low amplitudes 460A, 460B over time, the number of drops of fluid 340 over time can be determined.

As long as there is an output signal 430 with a pulse 460A, 460B occurring periodically over a predetermined period of time 240 (drop pulse detected), the pump 306 motor continues to operate 180. As discussed above, there are occasions when drops of the fluid 340 splash within the drip chamber 320 and cling to the drip chamber wall 400. If these drops are located in the Beam Path (BP), they will block the infrared beam and cause an interruption in the pulses (constant logic-low). If there is an interruption of the pulses 460A, 460B being monitored 240, there is a timeout 260 and the pump motor 306 is turned off 70. The timeout may vary from greater than or less than 3 seconds. Now, the infrared beam power is reset at the initial setting 60 and an infrared beam power update routine is run 80,160. Note, the timeout 260 will run a predetermined number of times to re-establish an output signal in the infrared beam detector 360. After the predetermined number of times, the pump motor 306 turns off 280 and the alarm will sound 300.

The infrared beam power update routine 80,160 consists of incrementally increasing a power level 80 of the infrared beam until the power level of the infrared beam is sufficient to re-establish an output signal at the infrared beam detector 160. The infrared beam power update routine 80 will cause the infrared beam power level to shift high enough to penetrate the drip chamber walls 400 and any standing water droplets formed that block the infrared beam. It should be noted the infrared beam power update routine 80 may be performed automatically and continuously by an algorithm.

When the output signal 430 of the infrared beam detector 360 is re-established after the infrared beam power update routine is run 80, 160, the pump motor 306 turns on 180. The infrared beam detector 360 continues to monitor the output signal 430 from the infrared beam emitter 380 as the fluid drips through the drip chamber 320 so as to detect pulses 460A, 460B in the output signal 240. When the delivery of all the fluid is complete 200, the pump motor 306 is turned off 220.

After each increase of the infrared beam power level 80 and a check of the logic state, the system checks if the maximum power 90 of the infrared beam is reached. If the maximum power of the infrared beam is achieved 90 and the output signal 430 cannot be re-established after a predetermined period of time 100, the pump motor 306 is shut off 120 and an alarm is triggered 140. In this manner, the method 10 of operation for the infrared drip sensor system allows the pump 306 to run without interruption of false alarms using the infrared beam power update routine 80, 160, but yet alarm when actual alarm conditions are met 140.

Figure 4:
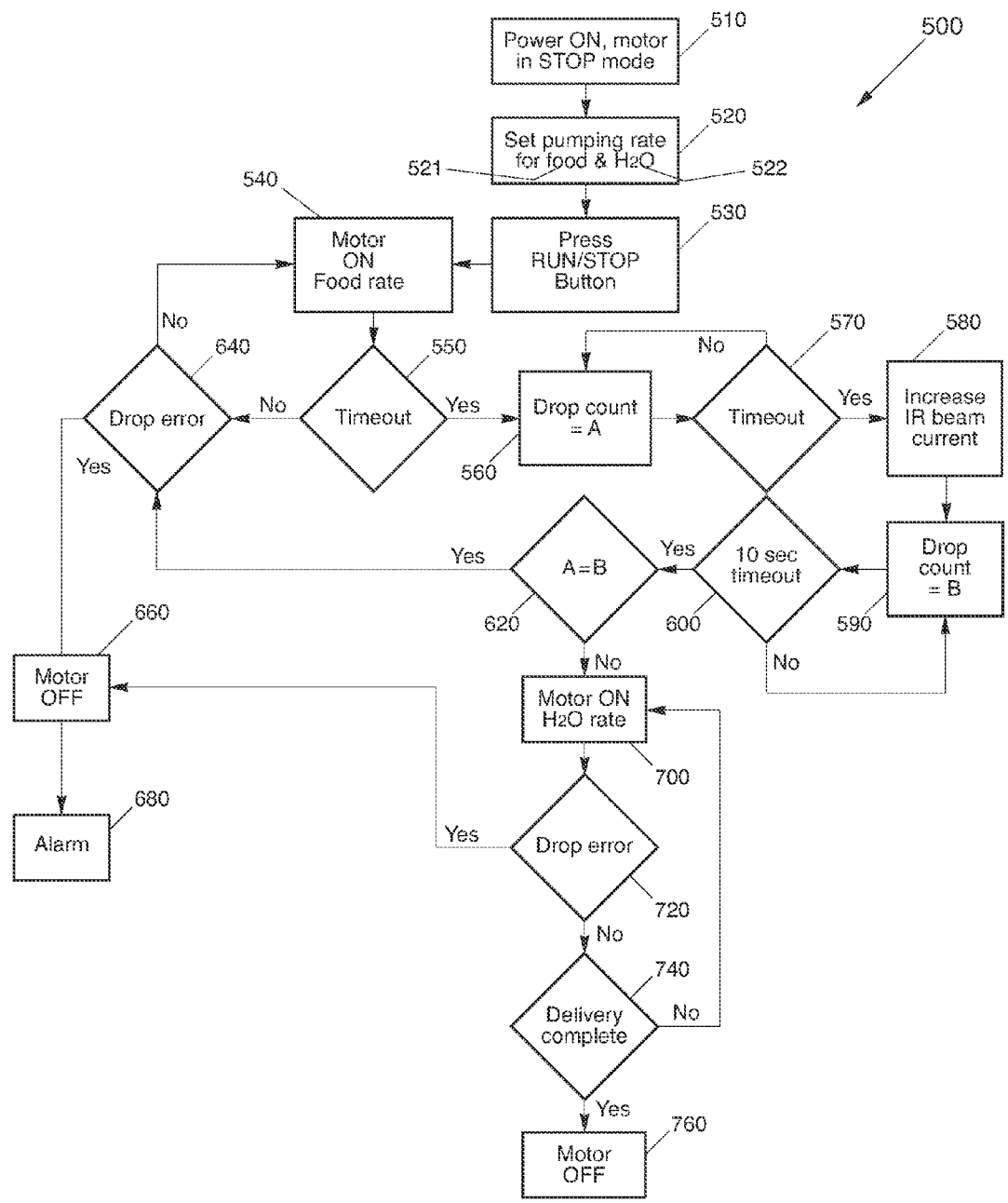
FIG. 4 is a flow chart of the method for automatic adjustment of the pumping rate of an eternal pump system according to the type of fluid flowing through the pump system.

Referring to FIG. 4, as a further improvement of the present invention, a method 500 for operating an infrared drop sensor system in an enteral pump system provides the ability to discern the difference between water and liquid nutrient. This method 500 permits the pumping of both liquid nutrient and water at user-programmed rates for each liquid. The method 500 for operating an infrared drop sensor system contains the following steps.

Figure 5:
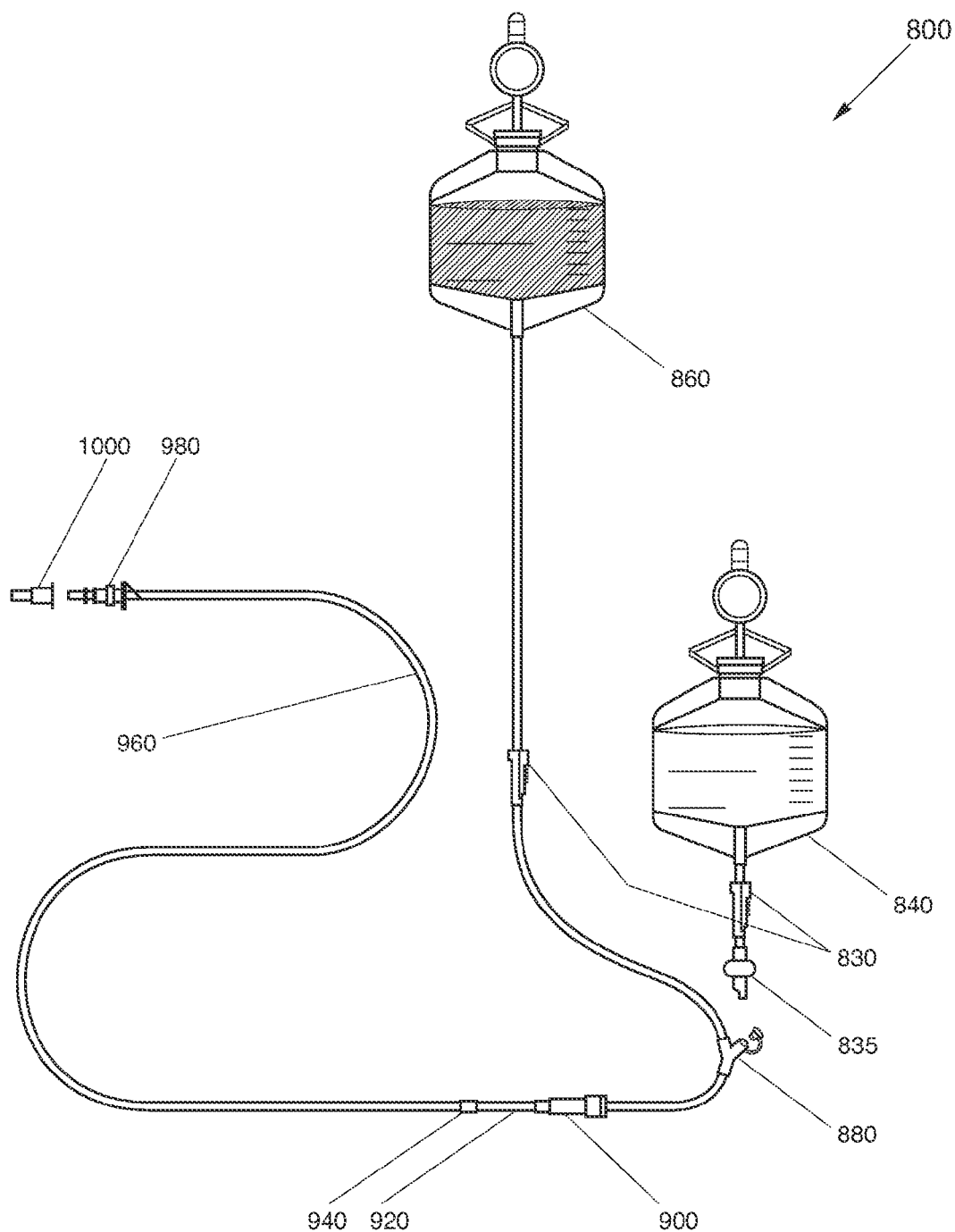
FIG. 5 is schematic illustration of a two-source tubing set for use in the method of FIG. 4 which provides both liquid nutrient and water.

Referring to FIG. 5, a first fluid 860 and a second fluid 840 are provided for pumping to the drip chamber 900. In one embodiment, the first fluid 860 is a liquid nutrient or nutritional supplement, which is typically opaque. The second fluid 840 is water or other type of clear fluid. An enteral tubing system 800 is also provided that first allows flow of the first fluid 860 and then flow of the second fluid 840 upon exhaustion of the first fluid 860. The enteral tubing system 800 will be described further herein.

A drip chamber 900 is provided which allows for the flow of the first fluid 860 and the second fluid 840 through the drip chamber 900. The drip chamber 900 has all of the features and advantages recited for the drip chamber 320 described above.

A pump 306 is provided which moves fluid through the enteral tubing system 800 and to the drip chamber 900. The pump 306 has the capability of having different pump rates depending upon the type of fluid moving through the drip chamber 900. For example, when the first fluid 860 is being pumped, a first pumping rate applies. When the second fluid 840 is being pumped, a second pumping rate applies. It should be noted that more than two fluids may be used with more than one programmed pumping rate for each type of fluid.

To begin operating the pump 306, as shown in the present method 500 of FIG. 4, the pump 306 is turned on with the pump motor 306 in stop mode 510. Next, a pumping rate is programmed at a first pumping rate 521 appropriate for the first fluid 860 to move the first fluid 860 to the drip chamber 900 wherein the first fluid 860 drips through the drip chamber 900 along a drip path DP 520. In addition, a pumping rate is also programmed for the second pumping rate 522 appropriate for the second fluid 840 to move the second fluid 840 to the drip chamber 900 wherein the second fluid 840 drips through the drip chamber 900 along a drip path DP 520.

Next, to begin operating the pump motor 306, the run button is pressed on the pump 306, 530. The first pumping rate 521 of the motor is set for the first fluid 860, 540. To measure the rate of drops through the drip chamber 900, an infrared sensor system similar to the infrared system 350 of FIG. 1 described above is used. The infrared beam detector 360 of the infrared system 350 generates an output signal 430 which is responsive to the presence of the infrared beam and generates a pulse 460A, 460B in the output signal 430 as the first fluid 860 drips through the drip chamber 900 640.

Similar to the infrared system 350 of FIG. 1, after setting an initial power level of the infrared beam, the output signal 430 of the infrared beam detector 360 is monitored as the fluid drips through the drip chamber 900 so as to detect pulses in the output signal. Note, if the first fluid 860 is opaque, the first fluid 860 will generate a pulse 460A, 460B in the output signal 430 as it passes through the drip chamber 900 along a DP with little to no sensitivity to the infrared beam power level. After a predetermined period of time of pumping the first fluid 860 drips through the drip chamber 900, a timeout occurs 550. If there are no pulses being detected over a pre-defined period of time 640, known as a drop error, the pump motor 306 is turned off 660 and the alarm is sounded 680. If there are pulses being detected over a predefined period of time, the pump motor 306 continues to run 540 at the predetermined rate for the first fluid 860.

At predetermined timeouts 550, a fluid type check routine runs to detect the type of fluid being pumped 560, 570, 580, 590, 600, 620. The fluid type check routine consists of counting a first number of pulses A over a predetermined period of time 560. At predetermined time intervals, a timeout is provided 570 after counting the first number of pulses A. At predetermined timeouts 570, the power level of the infrared beam is increased by a predetermined amount 570. In a preferred embodiment, the infrared beam power level is increased to a level sufficient for penetrating clear fluid such as water. At the increased power beam level, a second number of pulses B over a predetermined period of time is counted 590. At predetermined time intervals, a timeout is provided 600 after counting the second number of pulses B. At predetermined timeout 600, the first number of pulses A is compared to the second number of pulses B.

If the first number of pulses A is equal to the second number of pulses B, and there is no drop error 640, the pump motor 306 continues to operate at the first pumping rate 540. Since the first fluid 860 is opaque fluid such as liquid nutrition, the increase in the infrared beam power level will not penetrate through the fluid drop and thus will not increase or decrease the number of pulses in the output signal. By measuring the pulses over a defined period of time for two different infrared beam power levels, and the pulses are the same, it indicates the first fluid 860 has not been exhausted and should continue to be pumped at the first pumping rate.

If the first number of pulses A is unequal to the second number of pulses, the pump motor 306 switches to a second pumping rate for the second fluid 700. Since the second fluid 840 is clear, an increase in the infrared beam power level will now penetrate the water drops and change the number of pulses in the output signal. Preferably, if the infrared beam power level is increased sufficiently to penetrate second fluid 840 such as water, the infrared beam will pass through the second fluid 840 at the higher infrared beam power level. When measuring the second number of pulses B at a higher infrared beam power level, the infrared beam passes through the second fluid 840 so that fewer or no pulses will be counted. As a result, the second number of pulses B for the second fluid 840 will not equal the first number of pulses A. When A is not equal to B, the second fluid 840 is moving to the drip chamber 900 and a second pumping rate is turned on. By using a first pumping rate for the first fluid and a second pumping rate for the second fluid, the fluids, having different viscosity, can be delivered at the appropriate or desired rates. Of course, this method 500 may include more than two fluids and more than two rates of delivery of the fluids.

After the second pumping rate of the pump motor 306 is turned on for the second fluid 840, the pulses are monitored for a drop error 720. If a drop error occurs, the pump motor 306 is turned off 660 and the alarm will sound 680. If a drop error does not occur, and no pulses are being received by the infrared detector after a predetermined period of time, a check is run to see if the delivery of the second fluid 840 is complete 740. If the delivery of the second fluid 840 is complete, the pump motor 306 is turned off 760. If the delivery of the second fluid 840 is incomplete, the pump 306 continues to run at the second pumping rate.

The pumping rate will therefore automatically adjust to the programmed value, depending on the type of fluid flow. Thus, a patient may receive 500 milliliters (ml) of food at 125 ml/hr, followed by 500 ml of hydrating water at 290 ml/hr. The improvement is realized with no hardware modifications of the standard enteral pump, i.e. no additional pumping mechanisms, and with minimally expensive tubing set.

Referring to FIG. 5, the method 500 for operating an infrared drop sensor system in an enteral pump system utilizes a single motor enteral pump 306 with the above-described drop sensor system 350 and the tubing set 800 with two fluids, a first fluid 860 and a second fluid 840. Still referring to FIG. 5, these two fluids 840, 860 are coupled together at a Y-port 880 above the drip chamber 900. There is a low-cracking pressure check valve 835 (one-way check valve) in the second fluid tube that prevents backflow into the second fluid supply 840. The first fluid supply 860 is maintained at a height, which is above the top of the second fluid supply 840. This causes the check valve 835 to remain closed as long as there is a first fluid and thus keeps the second fluid from flowing. When the first fluid supply 860 becomes empty, the second fluid supply 840 begins to flow.

In addition to the components listed above for the tubing system 800, the following components are also part of the tubing system: roller clamps 830, elastomeric peristaltic tube section 920, tube adapter 940, plastic tubing 960, fitting for patient connection 980, and protective cap 1000.

Therefore, the present invention provides a method of operating an infrared drip sensor in an enteral pump system 10. The method of operating an infrared drip sensor allows for a reduction in false alarms. The present invention also provides a method for automatically adjusting the infrared beam power to accommodate water droplets and residue within the drip chamber. In addition, the present invention includes a method of operating a drip sensor to distinguish between water flow and liquid nutrient flow.

It would be appreciated by those skilled in the art that various changes and modifications can be made to the illustrated embodiments without departing from the spirit of the present invention. All such modifications and changes are intended to be covered by the appended claims and the present invention.

What is claimed is:

1. A method of operating an infrared drip sensor in an enteral pump system to reduce false alarm conditions, said method comprising the steps of:
    (a) providing a drip chamber;
    (b) operating a pump to move a fluid to said drip chamber wherein said fluid drips through said drip chamber along a drip path;

(c) optically coupling an infrared beam emitter with an infrared beam detector along an infrared beam path that extends through said drip chamber and intersects said drip path, said infrared beam emitter emitting an infrared beam, said infrared beam detector generating an output signal responsive to the presence of said infrared beam as said fluid drip through said drip chamber, (d) setting an initial power level of said infrared beam;

(e) monitoring said output signal of said infrared beam detector as said fluid drips through said drip chamber so as to detect pulses in said output signal level, said pulses representing said fluid dripping through said drip chamber;

(f) monitoring said pulses for an interruption thereof; and (g) running an infrared beam power update routine when an interruption is detected in said pulses, said infrared beam power update routine comprising the steps of incrementally increasing a power level of said infrared beam until said power level of said infrared beam is sufficient to re-establish an output signal at said infrared beam detector.

2. The method of operating an infrared drip sensor in an enteral pump system of claim 1, further comprising the steps of:

(h) shutting off motor for pump when said output signal cannot be reestablished after said infrared beam power update routine; and (i) triggering an alarm when said output signal cannot be reestablished after said infrared beam power update routine.

* * * * *